United States Patent [19]

Misra

[11] Patent Number: 4,814,454

[45] Date of Patent: Mar. 21, 1989

[54] QUINOLINE COMPOUNDS AND COMPOSITIONS THEREOF

[75] Inventor: Raj N. Misra, Hopewell, N.J.

[73] Assignee: E. R. Squibb & Sons, Inc., Princeton, N.J.

[21] Appl. No.: 64,716

[22] Filed: Jun. 22, 1987

Related U.S. Application Data

[62] Division of Ser. No. 791,964, Oct. 28, 1985, abandoned.

[51] Int. Cl.$^4$ .................. C07D 215/12; C07D 215/38
[52] U.S. Cl. ..................................... 546/171; 546/153; 546/168; 546/169; 546/175; 546/176
[58] Field of Search .................. 546/171, 176; 514/311

[56] References Cited

U.S. PATENT DOCUMENTS 2,886,436  5/1959  Schmidt et al. ................ 546/171 X

FOREIGN PATENT DOCUMENTS 0221677  5/1987  European Pat. Off. ............ 546/171

*Primary Examiner*—David B. Springer
*Attorney, Agent, or Firm*—Lawrence S. Levinson; Burton Rodney

[57] ABSTRACT p-Aminophenols are provided having the structure

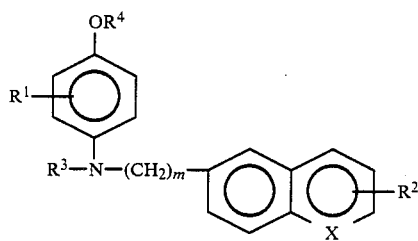

wherein m is 0 to 5; X is CH or N; $R^1$ and $R^2$ may be the same or different and are H, lower alkyl, aryl, hydroxy, hydroxyalkyleneoxy, alkylthio, alkoxy, alkanoyloxy, aryloxy, halo, carboxy, alkoxycarbonyl or amido; $R^3$ is H, lower alkyl, alkanoyl or aroyl; and $R^4$ is H, lower alkyl or alkanoyl, and including acid-addition salts thereof, with the proviso that when X is CH, m is 0 and $R^1$ is H, and when $R^4$ is H, $R^2$ is other than alkoxy, H or hydroxy, and when $R^4$ is benzoyl, $R^2$ is other than H.

These compounds together with the compounds defined in the above proviso are useful as inhibitors of leukotriene production and as such are useful as antiallergy, anti-inflammatory and anti-psoriatic agents.

6 Claims, No Drawings

QUINOLINE COMPOUNDS AND COMPOSITIONS THEREOF

This is a division of application Ser. No. 791,964, filed Oct. 28, 1985, abandoned.

DESCRIPTION OF THE INVENTION

The present invention relates to p-aminophenols and derivatives thereof which prevent leukotriene formation in macrophages and as such are useful, for example, as antiallergy agents, anti-inflammatory agents and in the treatment of psoriasis. These compounds have the structural formula

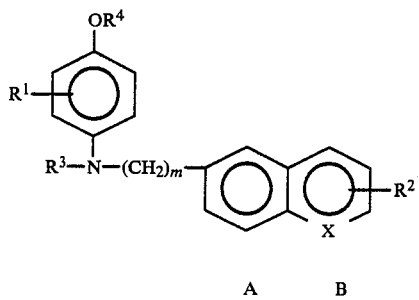

wherein m is 0 to 5; X is CH or N; $R^1$ and $R^2$ may be the same or different and may be H, lower alkyl, aryl, hydroxy, hydroxyalkyleneoxy, alkylthio, alkoxy, alkanoyloxy, aroyloxy, halo, carboxy, alkoxycarbonyl or amido; $R^2$ may be a substituent on either or both the A ring or B ring (with the B ring being preferred; $R^3$ is H, lower alkyl, alkanoyl or aroyl; and $R^4$ is H, lower alkyl or alkanoyl, and including pharmaceutically acceptable salts thereof, with the proviso that when X is CH, m is 0 and $R^1$ is H; when $R^4$ is H, $R^2$ is other than alkoxy, H or hydroxy; and when $R^4$ is benzoyl, $R^2$ is other than H.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids, (e.g., hydrochloric and hydrobromic acid), sulfuric acid, nitric acid and phosphoric acid, and organic acids such as maleic, fumaric, tartaric, citric, acetic, benzoic, 2-acetoxybenzoic, salicyclic; succinic acid, theophylline, 8-chlorotheophylline, p-aminobenzoic, p-acetamidobenzoic or methanesulfonic.

In addition, a method is provided for treating asthma mediated by leukotrienes in a mammalian species in need of such treatment, which method includes the step of administering to a mammalian host an effective amount of a compound of formula I or a pharmaceutically acceptable salt thereof or an N-naphthyl-p-aminophenol of the structure

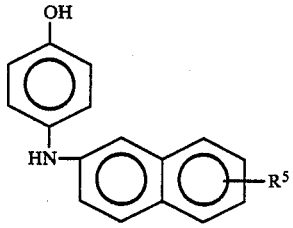

wherein $R^5$ is H, OH or alkoxy or an aminophenol of the structure

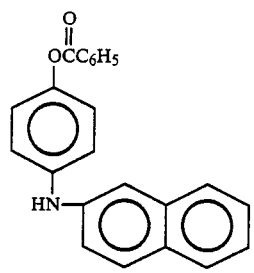

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups and/or 1 or 2 hydroxy groups.

The term "aralkyl", "aryl-alkyl" or "aryl-lower alkyl" as used herein refers to lower alkyl groups as discussed above having an aryl substituent, such as benzyl.

The term "halogen" or "halo" as used herein refers to chlorine, bromine, fluorine or iodine with chlorine being preferred.

The term "alkylthio" includes any of the above lower alkyl groups linked to a sulfur atom.

The term "hydroxyalkyleneoxy" refers to a group of the structure $HO-(CH_2)_n-O-$ wherein n is 2 to 8 and $(CH_2)_n$ is as defined below.

The terms "alkanoyl" and "aroyl" refer to a lower alkyl group linked to a carbonyl

group and an aryl group linked to a carbonyl group, respectively.

The terms "lower alkoxy", "alkoxy", "aralkoxy", "alkanoyloxy", and "aroyloxy" include any of the above lower alkyl, aralkyl, alkanoyl and aroyl groups linked to an oxygen atom.

The term "alkoxycarbonyl" refers to a group of the structure

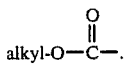

The term "amido" refers to

The terms $(CH_2)_m$ and $(CH_2)_n$ include straight or branched chain radicals having from 0 to 5 carbons in the normal chain in the case of $(CH_2)_m$, from 1 to 8 carbons in the normal chain in the case of $(CH_2)_n$ and may contain one or more lower alkyl and/or halogen substituents. Examples of $(CH_2)_m$ and $(CH_2)_n$ groups include $CH_2$,

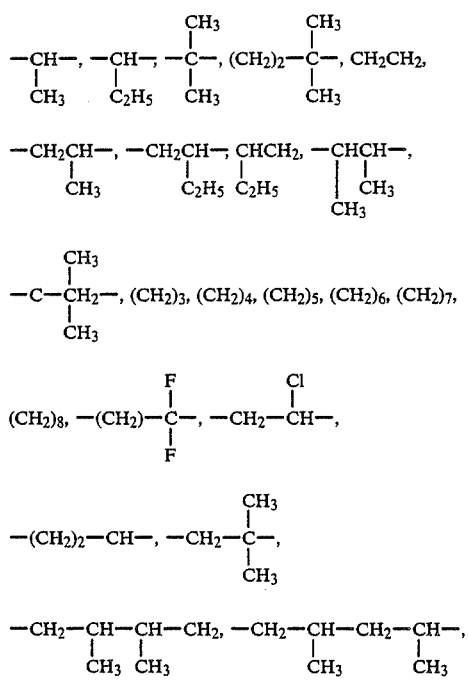

and the like.

Preferred compounds of the invention or for use in the method of the invention are those compounds wherein X is CH, m is 0, $R^4$ is H, $R^3$ is H, $R^2$ is in the B ring and is H, OH, halo such as Br or I, alkoxy, such as methoxy, lower alkyl such as n-pentyl, hydroxyalkyleneoxy, such as hydroxybutyleneoxy, alkylthio, such as methylthio, amino, carboxy, alkoxycarbonyl, such as methyloxycarbonyl; and wherein X is CH, m is 0, $R^4$ is H, $R^2$ is in the B ring and is OH or alkoxy, such as methoxy, and $R^3$ is alkyl, such as methyl; wherein X is CH, m is 1, $R^4$ is H, $R^3$ is H, and $R^2$ is H or OH; and wherein X is N, m is 0, $R^4$ is H and $R^2$ and $R^3$ are H.

The various compounds of the invention or compounds used in the method of the invention may be prepared as described below.

Thus, to form compounds of formula I and/or compounds employed in the method of the invention wherein $R^3$ is H, and m is 0, starting p-aminophenol compound A

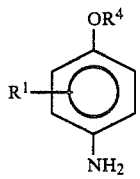

is reacted with compound B

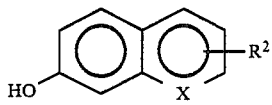

in the presence of aqueous sodium bisulfite in a closed vessel at from about 100° to about 175° C. to form compounds of the structure IV

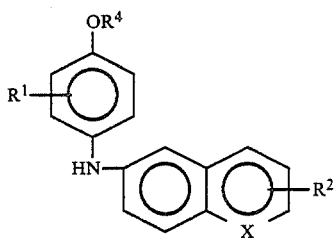

Compounds of the invention wherein m is 1 to 5 and $R^3$ is H may be prepared by reacting aminophenol A with a compound of the structure C

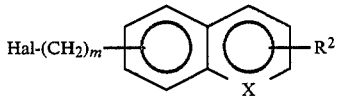

in the presence of weak base such as sodium bicarbonate, and hexamethylphosphoric triamide (HMPA) at temperatures of from about 0° to about 20° C. to form compounds of the structure V

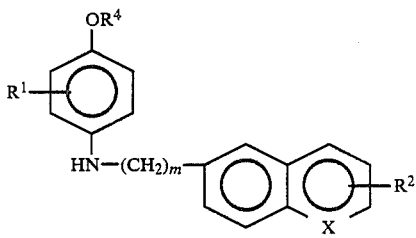

Compounds of the invention wherein $R^3$ is alkanoyl or aroyl may be prepared by reacting a compound of structure IV or V with the appropriate alkanoyl halide, such as acetyl chloride, or the appropriate aroyl halide, such as benzoyl chloride, in the presence of pyridine and methylene chloride to form compounds of the structure VI

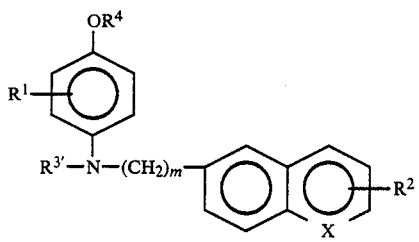

VI wherein R³' is alkanoyl or aroyl.

Compounds of the invention wherein R³ is lower alkyl may be prepared from compounds of formula IV or V. Where R⁴ in the formula IV or V compounds is H, then IV or V is treated with base such as sodium hydride and in the presence of tetrahydrofuran, benzene or ether and then after cessation of $H_2$ evolution, benzyl bromide (or other protecting agent) is added to form the protected compound VII

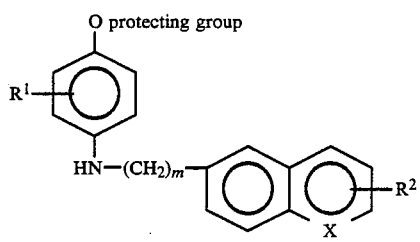

VII

Then, the protected compound VII or the formula IV or V compound wherein R⁴ is other than H is alkylated by reaction with an alkyl halide alkylating agent in the presence of sodium bicarbonate and hexamethylphosphoric triamide at elevated temperatures of from about 20° to about 80° C. to form the alkylated-protected compound VIII

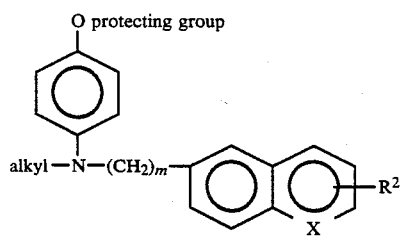

VIII which is then hydrogenated by treatment with $H_2$ in the presence of palladium on charcoal catalyst in acidic methanol to form the compound

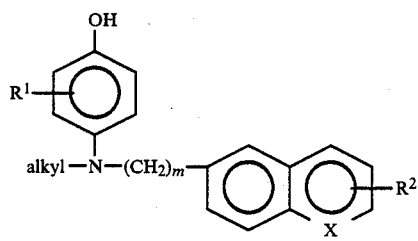

IX

Where R⁴ in the formulae IV or V compounds is other than H, then IV or V may be alkylated directly to form the formula X compound

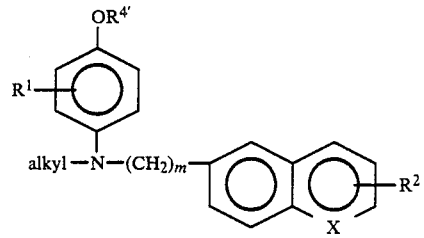

X (where R⁴' is alkyl, alkanoyl or aroyl).

The naphthalene derivatives employed as reactants with the aminophenol are commercially available, are known in the literature and/or generally may be prepared by conventional procedures. Thus, the naphthalene reactant B wherein X is CH, that is B'

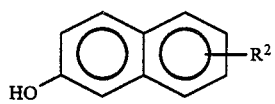

B' wherein R² is H, Br or OH at the 6-position are commercially available. Naphthalene reactants wherein R² is Cl, OCH₃ and CO₂H at the 2-position are known in the literature.

Naphthalene reactant B' wherein R² is —O(CH₂-)$_n$OH may be prepared by starting with the corresponding bromo-2-naphthol C

C which is dissolved in a dispersion of sodium hydride in tetrahydrofuran, cooled to 0° C. and then treated with alkenyl halide D

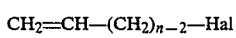

$CH_2=CH-(CH_2)_{n-2}-Hal$    D wherein Hal is Br or Cl in the presence of dimethylformamide to form the naphthalene XI

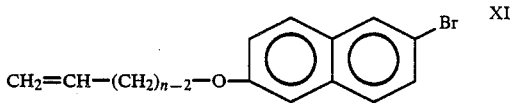

XI which is dissolved in tetrahydrofuran and then treated with t-C₄H₉Li at reduced temperature of, for example, from about −78° to about −20° C.

After warming to from about −20° C. to about 0° C., a solution of trimethyl borate in tetrahydrofuran is added and then acetic acid and hydrogen peroxide are added to form 2-naphthol derivative XII

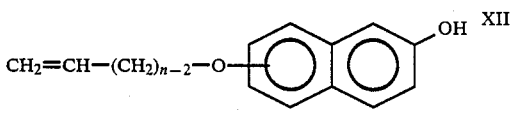

XII

Compound XII in hexane and tetrahydrofuran is treated with borane methyl sulfide complex; thereafter, ethanol, sodium hydroxide and hydrogen peroxide are added to form the 2-naphthalene XIII

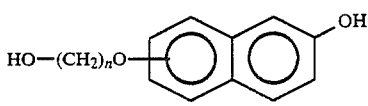

2-Naphthols of the structure XIV

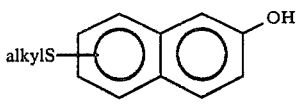

may be prepared by treating bromo-2-naphthol C with sodium hydride in the presence of tetrahydrofuran, and then adding a protecting compound such as bromomethyl methyl ether to form XV

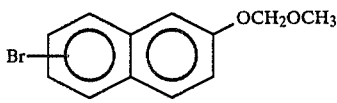

A solution of XV in ether and tetrahydrofuran is cooled to, for example, a reduced temperature of from about −78° to about −60° C. and t-butyllithium is added. Thereafter dialkyldisulfide E is added alkylSSalkyl    E The temperature is maintained at the above reduced temperature for about 30 minutes and then the reaction is warmed to room temperature to form XVI

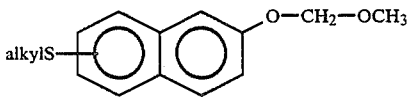

The protecting group is then removed by treating XVI in dioxane with aqueous hydrochloric acid to form XIV.

2-Naphthol compounds wherein $R^2$ is alkoxy may be prepared by treating bromonaphthol C' with sodium hydride

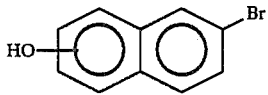

in the presence of tetrahydrofuran and then with an alkyl iodide in the presence of dimethylformamide to form XVII

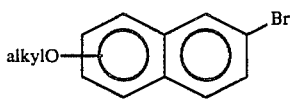

which is then treated sequentially with t-butyllithium in the presence of tetrahydrofuran, then trimethylborate, acetic acid and hydrogen peroxide, as described hereinbefore in the preparation of compound XII to form 2-naphthol compound XVIII

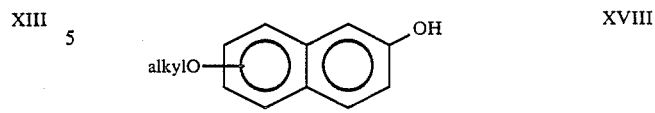

Naphthol XIX wherein $R^2$ is amido, that is

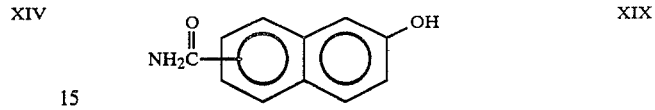

may be prepared by treating bromo-2-methoxynaphthalene, that is

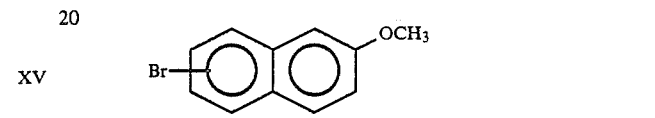

with t-butyllithium in the presence of tetrahydrofuran with $CO_2$ to form XX

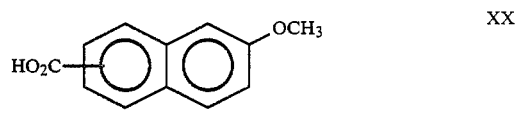

which in solution with dimethylformamide and tetrahydrofuran is cooled and treated with oxalyl chloride and ammonium hydroxide to form amino compound XXI

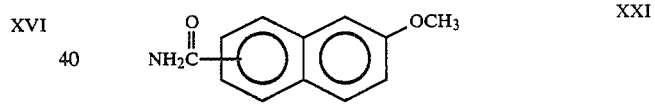

Amino compound is then converted to the 2-naphthol starting material XXII

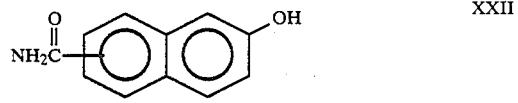

by treating XXI with boron tribromide ($BBr_3$) in the presence of methylene chloride while cooling to a temperature of from about −78° to about 20° C.

The compounds of the invention are inhibitors and prevent leukotriene formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C. TLC plates were visualized by spraying and heating with 5% phosphomolybdic acid in ethanol.

EXAMPLE 1

4-(2-Naphthalenylamino)phenol

A mixture of 1.00 g (6.94 mmol, Aldrich) of 2-naphthol, 1.01 g (9.26 mmol, Aldrich) of 4-aminophenol, and 5.2 g (50 mmol, Aldrich) of sodium bisulfite in 30 ml of $H_2O$ was refluxed for 36 hours. The reaction mixture was cooled, added to 50 ml of $H_2O$ and extracted with 50 ml of hot ethyl acetate. The organic layer was separated, washed with an additional 50 ml of $H_2O$, dried ($MgSO_4$) and concentrated in vacuo to give a solid. The crude solid was purified by flash chromatography (15×5.0 cm, 1:4 EtOAc/petroleum ether) followed by recrystallization (EtOAc/petroleum ether) to afford 1.15 g (71%) of title compound as pale purple flakes, m.p. 134°–135° C.

IR(KBr) 3401, 1631, 1597, 1515, 1314, 1245, 850, 827, 817, 739 $cm^{-1}$.

270 MHz $^1H$ NMR ($CDCl_3$/DMSO-$d_6$) 6.80 (dd, J=2, 7, 2H), 7.10 (m, 6H), 7.29 (dd, J=7, 8, 1H), 7.50 (d, J=8, 1H) 7.65 (m, 2H), 8.73 (s, 1H).

67.5 MHz $^{13}C$ NMR ($CDCl_3$/DMSO-$d_6$) 105.57, 114.91, 117.84, 120.94, 121.58, 124.76, 125.01, 126.35, 126.69, 127.58, 133.13, 133.80, 142.93, 151.85

MS(CI): 236 $(M+H)^+$.

TLC: Rf (silica gel, 1:2 EtOAc/pet ether)=0.44, PMA and UV. The Rf of 2-naphthol under identical conditions was 0.58.

Anal Calcd for $C_{16}H_{13}NO$: C, 81.68; H, 5.57; N, 5.95. Found: C, 81.68; H, 5.69; N, 6.02.

EXAMPLE 2

4-[(6-Methoxy-2-naphthyl)amino]phenol

A. 6-Methoxy-2-naphthol

The procedure used was described in *Org. Synthesis*, 49, 90 (1969).

The mixture of 590 mg (24.3 mmol, Aldrich) of magnesium turnings and 500 mg (2.11 mmol, Aldrich) of 2-bromo-6-methoxynaphthalene, in 10 ml of dry THF was heated until a reaction began. A solution of 4.50 g (19 mmol) of 2-bromo-6-methoxynaphthalene in 20 ml of THF was added to the reaction mixture over 15 minutes maintaining reflux with external heating when necessary. Refluxing was continued for an additional 30 minutes, then the resulting cooled solution was added dropwise to a solution of 2.6 ml (23 mmol, Alfa) of trimethylborate in 30 ml of dry THF which had been cooled to −10°. The reaction temperature was maintained below −5° during the addition. The white slurry which formed was stirred for 15 minutes then 1.8 ml (31 mmol) of glacial acetic acid was added in one portion followed by the dropwise addition of 4.8 ml of 15% aqueous hydrogen peroxide solution. The reaction mixture was warmed to room temperature, stirred for 30 minutes then added to 200 ml of 10% aqueous $NH_4Cl$ solution and extracted with 150 ml of ethyl acetate. The organic layer was separated, washed with an additional 150 ml of $H_2O$, dried ($MgSO_4$) and concentrated in vacuo to give a solid. The crude material was purified by flash chromatography (15×5.0 cm, 1:3 EtOAc/pet ether) and then recrystallized (EtOAc/pet ether) to afford 2.45 g (66%) of title alcohol as lusterous white plates, m.p. 145°–147°.

IR (KBr) 3304 (broad), 1609, 1512, 1453, 1388, 1251, 1231, 1155, 1112, 1031, 937, 851, 810 $cm^{-1}$.

MS(CI): 175 $(M+H)^+$.

B. 4-[(6-Methoxy-2-naphthyl)amino]phenol

A mixture of 300 mg (1.72 mmol) of Part A alcohol, 243 mg (2.23 mmol, Aldrich) of 4-aminophenol and 1.00 g (9.6 mmol) of sodium bisulfite in 5.0 ml of $H_2O$ was heated with stirring in a closed tube to 150° for 24 hours. The reaction mixture was cooled, added to 15 ml of ethyl acetate, washed with two 15 ml portions of $H_2O$, dried ($MgSO_4$) and concentrated in vacuo to give a solid. The crude solid was purified by flash chromatography (silica gel, 10×3.0 cm, 1:3 EtOAc/pet ether) then recrystallized (EtOAc/pet ether) to afford 260 mg (57%) of title compound as pink-tinged crystals, m.p. 153°–154°.

IR(KBr) 3417 (broad), 1608, 1508, 1389, 1311, 1251, 1231, 1216, 1160, 1024, 853 $cm^{-1}$.

270 MHz $^1H$ NMR ($CDCl_3$+DMSO-$d_6$) δ3.87 (s, 3H, —$OCH_3$), 6.83 (d, J=8, 2H), 6.90–7.21 (m, 6H), 7.48 (m, 1H), 7.57 (d, J=9, 1H), 8.43 (br s, 1H, —NH—).

MS(CI): 266 $(M+H)^+$.

TLC: Rf (silica gel, 1:3 EtOAc/pet ether)=0.19, PMA and UV, homogeneous.

Anal Calcd for $C_{17}H_{15}NO_2$: C, 76.96; H, 5.70; N, 5.28. Found: C, 77.00; H, 5.85; N, 5.19.

EXAMPLE 3

6-[(4-Hydroxyphenyl)amino]-2-naphthalenol

A mixture of 300 mg (2.75 mmol, Aldrich) of 4-aminophenol, 1.5 g (90%, 8.4 mmol, Aldrich) of 2,6-dihydroxynaphthalene and 1.0 g (9.6 mmol, Aldrich), of sodium bisulfite in 30 ml of $H_2O$ was refluxed for 18 hours. The reaction mixture was cooled, added to 30 ml of $H_2O$ and extracted with two 25 ml portions of ethyl acetate. The organic extracts were combined, dried ($MgSO_4$), and concentrated in vacuo to give a solid. The crude solid was purified by flash chromatography (15×5.0 cm, 1:2 EtOAc/pet ether) followed by recrystallization (EtOAc/pet ether) to afford 215 mg (31%) of title compound as pale pink crystals, m.p. 195°–196°.

IR(KBr) 3267 (broad), 1608, 1508, 1416, 1377, 1305, 1230, 1150, 1123, 945, 867, 825 $cm^{-1}$.

270 MHz $^1H$ NMR ($CDCl_3$+DMSO-$d_6$) 5.82 (s, 1H, —NH—), 6.82 (d, J=9, 2H, benzene aromatic), 6.90–7.20 (m, 6H, aromatic), 7.43 (d, J=8, 1H, naphthalene), 7.50 (d, J=8, 1H, naphthalene), 8.30 (s, 1H, —OH), 8.48 (s, 1H, —OH).

MS(CI): 252 (M+H)+.

TLC: Rf (silica gel, 1:2 EtOAc/pet ether)=0.14, PMA and UV, homogeneous.

The Rf of 2,6-dihydroxynaphthalene under identical conditions was 0.27.

Anal Cacld for $C_{16}H_{13}NO_3$: C, 76.48; H, 5.21; N, 5.57. Found: C, 76.68; H, 5.32; N, 5.65.

EXAMPLE 4

4-[(6-Butoxy-2-naphthalenyl)amino]phenol

A. 2-Bromo-6-butoxynaphthalene

An oil dispersion of 480 mg (50%, 10 mmol, Alfa) of sodium hydride was washed three times with petroleum ether then the residue covered with 5 ml of dry THF. To the resulting stirred slurry was added dropwise a solution of 2.00 g (8.97 mmol, Aldrich) of 6-bromo-2-naphthol, in 10 ml of THF over 10 minutes. The reaction mixture was stirred for 30 minutes then 1.70 g (9.23 mmol, Aldrich) of 1-iodobutane and 15 ml of sieve-dried DMF were added. The resulting solution was heated to 60° for two hours, then cooled, added to 100 ml of $H_2O$ and extracted with 50 ml of petroleum ether. The organic extract was washed with an additional 100 ml of $H_2O$, dried ($MgSO_4$) and concentrated in vacuo to give a solid. The crude material was purified by flash chromatography (15×5 cm, pet ether) to afford 2.31 g (92%) of title compound as a white solid, m.p. 48°-50°.

60 MHz $^1$H NMR (CDCl$_3$) 0.73–2.20 (m, 7H, —(CH$_2$)$_2$CH$_3$), 4.05 (t, J=6, 2H, —OCH$_2$—), 7.00–8.00 (m, 6H, aromatic).

TLC: Rf (silica gel, 1:9 Et$_2$O/pet ether)=0.63, PMA and UV, homogeneous.

B. 6-Butoxy-2-naphthol

To a solution of 500 mg (1.79 mmol) of Part A compound in 10 ml of dry THF at −78° was added 2.0 ml (1.8M in pentane, 3.6 mmol, Aldrich) of t-butyllithium solution over 10 minutes. The reaction mixture was stirred at −78° for 30 minutes, then at −20° for 15 minutes. To the resulting yellow slurry was added dropwise 230 ul (2.0 mmol, Alfa) of trimethylborate. The slurry became homogeneous and after 15 minutes, 114 ul (2.0 mmol) of glacial acetic acid was introduced followed by 0.50 ml (~2.2 mmol) of 15% aqueous $H_2O_2$. The reaction mixture was allowed to warm to room temperature over ~30 minutes, then added to 30 ml of 1M aqueous HCl solution and extracted with 25 ml of ethyl acetate. The organic extract was washed with an additional 30 ml of 1M aqueous HCl solution, dried (MgSO$_4$) and concentrated in vacuo to give a solid. The crude material was purified by flash chromatography (silica gel, 10×3.0 /cm, 1:4 EtOAc/pet ether) to afford 300 mg (78%) of title compound as a white solid, m.p. 100°-102°.

IR(KBr) 3286, 2959, 1610, 1514, 1390, 1254, 1230, 853 cm$^{-1}$.

60 MHz $^1$H NMR (CDCl$_3$) 0.70–2.15 (m, 7H, —(CH$_2$)$_2$CH$_3$), 4.00 (t, J=6, 2H, —OCH$_2$—), 4.78 (s, 1H, —OH), 6.80–7.80 (m, 6H, aromatic).

MS(CI): 217 (M+H)+.

TLC: Rf (silica gel, 1:9 EtOAc/pet ether)=0.15, PMA and UV, homogeneous.

C. 4-[6-Butoxy-2-naphthalenyl)amino]phenol

A mixture of 270 mg (1.25 mmol) of Part B compound 218 mg (2.00 mmol, Aldrich) of 4-aminophenol and 500 mg (4.81 mmol, Aldrich) of sodium bisulfite in 5 ml of 1:4 EtOH/H$_2$O was stirred rapidly in a sealed tube at 170° for 48 hours. The reaction mixture was cooled, added to 25 ml of H$_2$O and extracted with two 20 ml portions of ethyl acetate. The combined organic extracts were dried (MgSO$_4$) and concentrated in vacuo to give a solid. The crude material was purified by flash chromatography (silica gel 9.0×5.0 cm, 1:5 EtOAc/pet ether) followed by recrystallization (ether/pet ether) to afford 160 mg (42%) of title compound as small chalk-white crystals, m.p. 138°-139°.

IR(KBr) 3415, 3290 (broad), 2959, 1609, 1512, 1391, 1247, 1189, 1162, 854, 838, 823 cm$^{-1}$.

270 MHz $^1$H NMR (CDCl$_3$) 0.99 (t, J=7, 3H, —CH$_3$), 1.53 (tq, J=7, 7, 2H, —CH$_2$CH$_3$), 1.82 (tt, J=7, 7, 2H, —OCH$_2$CH$_2$—), 4.05 (t, J=7, 2H, —OCH$_2$—), 4.65 (br s, 1H, —OH), 6.80 (d, J=8, 2H, phenyl protons), 7.20 (m, 7H, aromatic), 7.50 (broad d, J=8, 1H, aromatic), 7.59 (d, J=8, 1H, aromatic).

MS(CI): 308 (M+H)+.

TLC: Rf (silica gel, 1:2 EtOAc/pet ether)=0.43, PMA and UV, homogeneous. The Rf of Part B naphthol under similar conditions was 0.60.

Anal Calcd for $C_{20}H_{21}NO_2$: C, 78.15; H, 6.89; N, 4.56. Found: C, 78.13; H, 7.05; N, 4.49.

EXAMPLE 5

4-[[6-(Methylthio)-2-naphthalenyl]amino]phenol

A. 6-Bromo-2-methoxymethyleneoxynaphthalene

The oil was removed from 1.2 g (50% in oil, 25 mmol, Alfa) of sodium hydride dispersion by three washes with petroleum ether then 50 ml of dry THF was added to the residue. To the resulting stirred suspension of sodium hydride was introduced in portions a total of 5.00 g (22.4 mmol, Aldrich) of 6-bromo-2-naphthol, over 30 minutes. The reaction mixture was stirred for an additional 30 minutes then 2.0 ml (24 mmol, Aldrich) of bromomethyl methyl ether was added dropwise over 15 minutes. After 30 minutes, the reaction mixture was added to 200 ml of H$_2$O and extracted with two 75 ml portions of ethyl acetate. The organic extracts were combined, dried (MgSO$_4$) and concentrated in vacuo to give a solid. The crude solid was purified by flash chromatography (20×5.0 cm, 1:15 EtOAc/pet ether) to afford 5.55 g (93%) of title compound as a pale yellow solid, m.p. 63°-65°.

IR (KBr) 2958, 1622, 1589, 1497, 1383, 1254, 1200, 1158, 1079, 1000 cm$^{-1}$.

60 MHz $^1$H NMR(CDCl$_3$) 3.50 (s, 3H, —OCH$_3$), 5.27 (s, 2H, —OCH$_2$O—), 7.03–8.00 (m, 6H, aromatic).

TLC: Rf (silica gel, 1:4 EtOAc/pet ether)=0.53, PMA and UV.

The Rf of 6-bromo-2-naphthol under identical conditions was 0.26.

B. 6-Methylthio-2-methoxymethyleneoxynaphthalene

To a solution of 2.67 g (10.0 mmol) of Part A compound in 30 ml of dry ether and 10 ml of dry THF at −78° was added dropwise 14 ml (1.4M in pentane, 20 mmol, Aldrich) of t-butyllithium solution over 20 minutes. The reaction mixture was stirred at −78° for 30 minutes then at −20° for 30 minutes. The resulting slurry was recooled to −78° and 1.1 ml (12 mmol, distilled) of dimethyl disulfide was introduced in one portion. The reaction mixture was stirred at −78° for 30 minutes, warmed to room temperature over 2 hours then added to 50 ml of 1M aqueous NaOH and extracted with 50 ml of ethyl acetate. The organic extract was washed with an additional 50 ml of 1M aqueous NaOH, dried (MgSO$_4$) and concentrated in vacuo to give a yellow solid. The crude material was purified by flash chromatography (15×5.0 cm, 1:20 ether/pet ether) then recrystallized (ether/pet ether) to afford 1.40 g (60%) of title compound as white crystals, m.p. 58°–60°.

IR (KBr) 2967, 1593, 1494, 1380, 1252, 1214, 1194, 1159, 1079, 1070, 993 cm$^{-1}$.

60 MHz $^1$H NMR (CDCl$_3$) 2.55 (s, 3H, —SCH$_3$), 3.50 (s, 3H, —OCH$_3$), 5.27 (s, 2H, —OCH$_2$O—), 7.07–7.80 (m, 6H, aromatic).

TLC: Rf (silica gel, 1:9 ether/pet ether)=0.38, PMA and UV, co-spots with Part A compound under these conditions.

C. 6-Methylthio-2-naphthol

To a solution of 700 mg (2.99 mmol) of Part B compound in 4 ml of dioxane was added 1 ml of 1M aqueous HCl and heated to 50° for 18 hours. The reaction mixture was cooled, added to 50 ml of H$_2$O and extracted with two 25 ml portions of ethyl acetate. The organic extracts were combined, dried (MgSO$_4$) and concentrated in vacuo to give a solid. The crude solid was purified by flash chromatography (10×5.0 cm, 1:6 EtOAc/pet ether) to afford 165 mg (29%) of title compound as a white solid, m.p. 120°–122°.

IR(KBr) 3335 (broad), 1599, 1573, 1501, 1432, 1354, 1278, 1210, 916, 863, 813 cm$^{-1}$.

270 MHz $^1$H NMR(CDCl$_3$) 2.55 (s, 3H, —SCH$_3$H), 4.92 (s, 1H, —OH), 7.10 (m, 2H, aromatic), 7.35 (dd, J=2, 9, 1H, aromatic), 7.60 (m, 3H, aromatic).

MS(CI): 191 (M+H)$^+$.

TLC: Rf (silica gel, 1:4 EtOAc/pet ether)=0.37, PMA and UV. The Rf of Part B compound under identical conditions was 0.68.

D. 4-[[6-(Methylthio)-2-naphthalenyl]-amino]phenol

A mixture of 150 mg (0.79 mmol) of Part C naphthol, 170 ml (1.56 mmol, Aldrich) of 4-aminophenol, 500 mg (4.88 mmol, Aldrich) of sodium bisulfite and 5 ml of H$_2$O was stirred rapidly in a sealed tube at 155°–160° for 60 hours. The reaction mixture was cooled, added to 25 ml of H$_2$O and extracted with two 25 ml portions of ethyl acetate. The combined organic extracts were dried (MgSO$_4$) and concentrated in vacuo to give a solid. The crude material was purified by flash chromatography (12×3.0 cm, 1:3 EtOAC/pet ether) followed by recrystallization (EtOAc/pet ether) to afford 149 mg (67%) of title compound as light grey crystals, m.p. 127°–128°.

IR(KBr) 3410, 3289 (broad), 1629, 1593, 1518, 1503, 1441, 1311, 1234, 858, 815 cm$^{-1}$.

270 MHz $^1$H NMR(CDCl$_3$) 2.54 (s, 3H, —SCH$_3$), 4.58 (s, 1H, —OH), 5.60 (s, 1H, —NH—), 6.82 (d, J=9, 2H, benzene aromatics), 7.09 (d, J=9, 3H, benzene aromatics), 7.14 (d, J=2, 1H), 7.30 (dd, J=2, 9, 1H), 7.50 (d, J=9, 1H), 7.55 (d, J=2, 1H), 7.60 (d, J=9, 1H).

MS(CI): 282 (M+H)$^+$

TLC: Rf (silica gel, 1:3 EtOAc/pet ether)=0.19, PMA and UV, homogeneous.

The Rf of Part C compound under identical conditions was 0.34.

Anal Calcd for C$_{17}$H$_{15}$NOS: C, 72.57; H, 5.37; N, 4.98; S, 11.40. Found: C, 72.65; H, 5.20; N, 4.92; S, 11.18.

EXAMPLE 6

4-[[6-[(4-Hydroxyphenyl)amino]-2-naphthalenyl]oxy]-butanol

A. 6-Bromo-2-(2-propenyloxy)naphthalene

A solution of 10.00 g (45 mmol, Aldrich) of 6-bromo-2-naphthol and 2.16 g (49.0 mmol, 1.1 eq. 60% in oil, Aldrich) of NaH dispersion in 100 ml of dry THF was stirred at 0° C., until gas evolution ceased. A solution of 4.60 ml (45.0 mmol, Aldrich) of 4-bromo-1-butene in 25 ml of DMF was added dropwise and the solution was warmed to room temperature, then stirred at 70° C. overnight. To this solution was added 2.28 ml (22.5 mmol, 0.5 eq., Aldrich) of 4-bromo-1-butene and 6 ml of hexamethylphosphoric triamide (HMPA). Then 1.00 g (20.8 mmol, 60% in oil, Aldrich) of NaH dispersion in 10 ml of dry THF was added, stirred at 70° C. for 8 hours and finally heated to 90° C. for 12 hours. The mixture was cooled, water was added, this was extracted with EtOAc, dried (MgSO$_4$) and concentrated in vacuo. Purification was achieved via flash chromatography (silica gel, 1:8 EtOAc/petroleum ether) to yield 4.31 g (35%) of title compound as a bright yellow solid, m.p. 35°–37° C.

IR(KBr) 3474, 3077, 2926, 1627, 1591, 1498, 1459, 1388, 1262, 1207, 1168, 1125, 1064, 1032, 988, 921, 877 cm$^{-1}$.

270 MHz $^1$H NMR(CDCl$_3$) δ2.61 (dt, J=6, 7 Hz, 2H, —OCH$_2$CH$_2$), 4.12 (t, J=7 Hz, 2H, —OCH$_2$CH$_2$—), 5.18 (m, 2H, —CH=CH—(CH$_2$)$_2$—O—), 5.94 (ddt, J=6, 7 Hz, 1H, —CH$_2$=CH—(CH$_2$)$_2$—O—), 7.09 (d, J=3 Hz, 1H, aromatic H), 7.16 (dd, J=3, 9 Hz, 2H, aromatic H's), 7.48 (dd, J=2, 6 Hz, 1H, aromatic H's), 7.58 (d, J=9 Hz, 1H, aromatic H), 7.63 (d, J=9 Hz, 1H, aromatic H), 7.90 (s, 1H, aromatic H).

TLC: Rf (silica gel, 1:1 EtOAc/petroleum ether)=0.78, UV and PMA, homogeneous.

B. 6-(2-Propenyloxy)-2-naphthol

To a solution of 5.33 g (19.2 mmol) of Part A compound in 20 ml of dry THF at −78° C. was added 23.3 ml (42.3 mmol, 2.2 eq., 1.82M in pentane, Aldrich) of t-BuLi over 20 minutes. After 30 minutes, the solution was warmed to −20° C., stirred for 15 minutes then a solution of 2.40 ml (23.0 mmol, 1.2 eq., Alfa) of trimethylborate in 5 ml of dry THF was added. After 15 minutes, 1.7 ml (29 mmol) of glacial acetic acid was added, followed by 2.30 ml (23.0 mmol, 1.2 eq.) of 30% aqueous H$_2$O$_2$ in 3 ml of H$_2$O. The resulting mixture was warmed to room temperature and stirred for 30 minutes. To this was added 10% aqueous NH$_4$Cl and this was extracted with EtOAc. The organic layer was washed with H$_2$O, dried (MgSO$_4$) and concentrated in vacuo. Purification was accomplished via flash chromatography (silica gel, 1:6, 1:8 EtOAc/petroleum ether) and washing with petroleum ether to afford 2.04 g (50%) of title compound as lustrous white crystals: m.p. 92°–93° C.

IR(KBr) 3262, 1607, 1513, 1388, 1233, 1155, 1113, 1032, 951, 916, 852, 810 cm$^{-1}$.

270 MHz $^1$H NMR(CDCl$_3$) δ2.60 (dt, J=5, 5 Hz, 2H, —OCH$_2$CH$_2$—), 4.11 (t, J=5 Hz, 2H, OCH$_2$CH$_2$—), 4.86 (s, 1H, —OH), 5.12 (m, 2H, CH$_2$=CH—) 5.94 (ddt, J=6, 5, 3 Hz, 1H, CH$_2$=CH—), 7.06 (m, 4H, aromatic H's), 7.56 and 7.63 (two d's overlapping, J=6 Hz, 2H, aromatic H's).

MS(CI): 215 (M+H)$^+$.

TLC: Rf (silica gel, 1:1 EtOAc/petroleum ether)=0.61, UV and PMA, homogeneous.

C. 6-(4-Hydroxybutoxy)-2-naphthol

A solution of 720 mg (3.4 mmol) of Part A compound in 5 ml of hexanes and 2 ml of dry THF was cooled to 0° C. and 0.14 ml (10M, 0.4 eq., 1.4 mmol, Aldrich) of borane methyl sulfide complex was added. The resulting slurry was warmed to room temperature and stirred. During 1 hour, an additional 2 ml of dry THF and 70 ul (10M, 0.7 mmol, Aldrich) of borane methyl sulfide complex were added. After 1.5 hours, another 70 ul (0.2 eq., 10M, 0.7 mmol, Aldrich) of borane methyl sulfide complex was added. After one hour, 2 ml of EtOH was added, followed by 2 ml of 3N NaOH and then the solution was cooled to 0° C. To this was slowly added 700 μl (7.2 mmol, 1.05 eq.) of 30% aqueous $H_2O_2$ and the solution was refluxed for 1 hour. The solution was cooled, EtOAc was added and this was washed with brine, dried ($MgSO_4$) and concentrated in vacuo. The aqueous layers were acidified using concentrated HCl, combined and then extracted with EtOAc. The organic layers were combined, dried ($MgSO_4$) and concentrated in vacuo. Final purification was achieved via flash chromatography (silica gel, 1:4, 1:2 EtOAc/petroleum ether) to yield 289 mg (37%) of title compound as a white solid, m.p. 148°–150° C.

IR(KBr) 3365, 3084, 2951, 1605, 1513, 1445, 1391, 1228, 1158, 1050, 961, 863, 853, 806 $cm^{-1}$.

270 MHz $^1H$ NMR($CDCl_3$) δ1.75 (dt, J=7, 7 Hz, 2H, $HOCH_2CH_2$—), 1.85 (dt, J=7, 7 Hz, 2H, —$CH_2CH_2OR$), 3.71 (t, J=7 Hz, 2H, —$CH_2OH$), 4.08 (t, J7 Hz, 2H, —$CH_2CH_2OR$), 7.07 (m, 4H, aromatic H's), 7.57 (t, J=8 Hz, 2H, aromatic H's).

TLC: Rf (silica gel, 1:1 EtOAc/petroleum ether)=0.21, UV and PMA.

D. 4-[[6-[(4-Hydroxyphenyl)amino]-2-naphthalenyl]oxy]butanol

A rapidly stirred solution of 290 mg (1.3 mmol) of Part B compound, 283 mg (2.60 mmol, 2 eq., Aldrich) of 4-aminophenol and 500 mg (4.8 mmol, 3.7 eq.) of sodium bisulfite in 5 ml of $H_2O$ was heated in a sealed tube to 150° C. for 19 hours. The solution was cooled, water was added and this was extracted with EtOAc. The organic layers were combined, dried ($MgSO_4$) and concentrated in vacuo. Initial purification was accomplished via flash chromatography (silica gel, 1:2, THF/petroleum ether). The resulting product contaminated with Part C compound was washed with 0.1N NaOH, followed by $H_2O$. Final purification via flash chromatography (1:3 THF/petroleum ether) yielded 180 mg (43%) of title compound as a light purple solid, m.p. 132°–135° C.

IR(KBr) 3421, 2947, 1608, 1509, 1389, 1316, 1249, 1163, 1047, 1003, 952, 857, 818 $cm^{-1}$.

270 MHz $^1H$ NMR(DMSO-$d_6$) δ1.60 (dt, J=6, 6 Hz, 2H, —$CH_2CH_2OH$), 1.78 (dt, J=6, 6 Hz, 2H, —$OCH_2CH_2$—), 3.47 (dt, J=6, 6 Hz, 2H, —$CH_2OH$), 4.02 (t, J=6 Hz, 2H, —$OCH_2CH_2$—), 4.43 (t, J=6 Hz, 1H, —$CH_2OH$), 6.72 (d, J=8 Hz, 2H), 7.00 (d, J=8 Hz, 3H), 7.13 (m, 3H), 7.50 (d, J=9 Hz, 1H), 7.59 (d, J=8 Hz, 1H), 8.97 (s, 1H, —OH or NH).

MS(CI): 324 (M+H)+.

TLC: Rf (silica gel, 1:1 EtOAc/petroleum ether)=0.36, UV and PMA, homogeneous.

Anal Calcd for $C_{20}H_{21}NO_3$: C, 74.28; H, 6.55; N, 4.33. Found: C, 73.99; H, 6.55; N, 4.35.

EXAMPLE 7

6-[(4-Methoxyphenyl)amino]-2-naphthalenol

A solution of 1.00 g (8.1 mmol, Aldrich) of p-anisidine, 5.20 g (32.5 mmol, 4 eq., Aldrich) of 2,6-dihydronaphthalene and 3.38 g (32.5 mmol, 4 eq., Aldrich) of sodium bisulfite in 60 ml of $H_2O$ was refluxed for 12 hours. The reaction was cooled to room temperature, extracted with EtOAc, dried ($MgSO_4$) and concentrated in vacuo. Initial purification was accomplished via flash chromatography (1:6, 1:4 EtOAc/petroleum ether) and then concentration of appropriate fractions. Ethyl acetate was added, this was washed repeatedly with warm 0.1N NaOH to remove 2,6-dihydroxynaphthalene, dried ($MgSO_4$) and concentrated in vacuo. Final purification by flash chromatography (1:4 THF/petroleum ether) yielded 633 mg (30%) of title compound as a muddy pink solid, m.p. 152°–153° C.

IR(KBr) 3419, 3374, 1610, 1504, 1318, 1267, 1227, 1183, 1148, 1125, 1023, 946, 866 $cm^{-1}$.

270 MHz $^1H$ NMR ($CDCl_3 + CD_3OD$) 3.80 (s, 3H, $OCH_3$), 6.87 (d, J=9 Hz, 2H, aromatic H's), 7.01–7.12 (m, 5H, aromatic H's), 7.22 (s, 1H, aromatic H's), 7.48 (d, J=8 Hz, 1H, aromatic H's), 7.53 (d, J=9 Hz, 1H, aromatic H's).

MS(CI): 266 (M+H)+.

TLC: Rf (silica gel, 1:1 EtOAc/petroleum ether)=0.50, UV and PMA, homogeneous.

Anal Calcd for $C_{17}H_{15}NO_2$: C, 76.96; H, 5.71; N, 5.28. Found: C, 76.74; H, 5.86; N, 5.22.

EXAMPLE 8

6-[(4-Hydroxyphenyl)amino]naphthalene-2-amide

A. 6-Methoxy-2-naphthalene carboxylic acid

A solution of 8.00 g (33.8 mmol, Aldrich) of 6-bromo-2-methoxynaphthalene in 75 ml of dry THF was cooled to −78° C. and 36 ml (1.8M in pentane, 65 mmol, Aldrich) of t-butyllithium was added over 30 minutes. The reaction mixture was stirred for 30 minutes at −78° C. then warmed to −20° C. for 30 minutes. The mixture was recooled to −78° C. and b 8.00 g (180 mmol) of crushed dry ice was added to the slurry, and then this was allowed to warm to room temperature over 2 hours. The mixture was concentrated in vacuo, 100 ml of 1N HCl was added to the residue and this was extracted with 100 ml of hot EtOAc. The organic layer was washed with water, dried ($MgSO_4$) and concentrated in vacuo to give a solid. Purification via recrystallization (EtOAc/petroleum ether) afforded 5.80 g (85%) of the title compound as small white needles: m.p. 198°–200° C.

IR(KBr) 3449, 2968, 2941, 1683, 1626, 1483, 1300, 1257, 1209, 1031, 860 $cm^{-1}$.

270 MHz $^1H$ NMR(DMSO-$d_6$) δ3.91 (s, 3H, —$OCH_3$), 7.24 (d, J=9 Hz, 1H, aromatic H), 7.39 (s, 1H, aromatic H), 7.90 (dd, J=8, 8 Hz, 2H, aromatic H's), 8.01 (d, J=9 Hz, 1H, aromatic H), 8.51 (s, 1H, aromatic H).

TLC: Rf (1:1 EtOAc/petroleum ether)=0.37, UV and PMA.

B. 6-Methoxy-2-naphthaleneamide

A solution of 750 mg (3.71 mmol) of Part A compound and 3 drops of DMF in 10 ml of dry THF was cooled to 0° C., then 490 ul (5.60 mmol, 1.5 eg., Aldrich) of oxalyl chloride was slowly added. After 45 minutes the reaction mixture was slowly added to 10 ml of 10% aqueous NH$_4$OH at 0° C., then the solution was warmed to room temperature and stirred for 2 hours. To this was added 1N aqueous HCl, and extracted with warm EtOAc. The organic layers were warmed, filtered through a small pad of MgSO$_4$ and concentrated in vacuo. Purification via recrystallization (EtOAc/EtOH/petroleum ether) afforded 480 mg (64%) of title compound as white lustrous needles: m.p. 224°–226° C.

IR(KBr) 3379, 3198, 1656, 1627, 1599, 1484, 1391, 1263, 1220, 1030, 916, 863, 818 cm$^{-1}$.

270 MHz $^1$H NMR (DMSO-d$_6$) δ3.90 (s, 3H, —OCH$_3$), 7.23 (d, J=8 Hz, 1H, aromatic H), 7.37 (m, 2H, aromatic H's, amide H), 7.87 (m, 4H, aromatic H's, amide H), 8.40 (s, 1H, aromatic H).

TLC: Rf (1:9 MeOH/CH$_2$Cl$_2$)=0.34, UV only.

C. 6-Hydroxy-2-naphthaleneamide

A solution of 470 mg (2.34 mmol) of Part B compound in 5 ml of dry CH$_2$Cl$_2$ was cooled to −78° C. and 2.60 ml (1M in CH$_2$Cl$_2$, Aldrich, 2.60 mmol) of BBr$_3$ was added. The solution was warmed to room temperature, stirred for 2.5 hours then re-cooled to −78° C. To this solution was added another 2.60 ml (1M in CH$_2$Cl$_2$, Aldrich, 2.60 mmol) of BBr$_3$ then warmed to 0° C., stirred for 15 minutes and finally warmed to room temperature. The solution was stirred for 12 hours at room temperature, then slowly poured into 50 ml of saturated aqueous NaHCO$_3$ and extracted with two 30 ml portions of EtOAc. The organic layers were combined, washed with H$_2$O, then brine, dried (MgSO$_4$) and concentrated in vacuo. Purification was achieved via recrystallization (EtOAc/petroleum ether) to yield 343 mg (78%) of title compound as a yellow solid: m.p. 205°–206° C.

IR(KBr) 3403, 3217, 1648, 1602, 1485, 1298, 1221, 1157, 924, 871, 817 cm$^{-1}$.

270 MHz $^1$H NMR(DMSO-d$_6$) δ7.13 (d, J=8 Hz, 2H, aromatic H's), 7.26 (s, 1H, —NH—), 7.69 (d, J=8 Hz, 1H, aromatic H), 7.83 (d, J=8 Hz, 2H, aromatic H's), 7.95 (s, 1H, —NH—), 8.33 (s, 1H, aromatic H), 9.44 (s, 1H, —OH).

TLC: Rf (1:9 MeOH/CH$_2$Cl$_2$)=0.19 UV and PMA.

D. 6-[(4-Hydroxyphenyl)amino]naphthalene-2-amide

A solution of 320 mg (1.71 mmol) of Part C compound, 373 mg (3.42 mmol, 2 eq., Aldrich) of 4-aminophenol and 0.5 g (4.8 mmol) of sodium bisulfite in 5 ml of H$_2$O was heated to 150° C. in a sealed tube for 17 hours. Then another 373 mg (3.42 mmol, 2 eq., Aldrich) of 4-aminophenol was added and heating at 150° C. in a sealed tube was continued for 16 hours. The solution was cooled, added to H$_2$O and this solution was extracted with EtOAc. The organic layers were combined, washed with brine, dried (MgSO$_4$) and concentrated in vacuo. Purification via flash chromatography (silica gel, 2:3 THF/petroleum ether) then recrystallization (aqueous MeOH) afforded 129 mg (27%) of title compound as an orange solid: m.p. 260° C.

IR(KBr) 3437, 3197, 1668, 1626, 1592, 1512, 1497, 1402, 1321, 1241, 1170, 1145, 1104, 812 cm$^{-1}$.

270 $^1$H NMR(DMSO-d$_6$) δ6.48 (s, 1H, amine-NH— or —OH), 6.77 (d, J=8 Hz, 2H, phenol H's), 7.13 (m, 4H, aromatic H's, amide H, phenol H's), 7.56 (d, J=9 Hz, 1H, aromatic H's), 7.75 (m, 2H, aromatic H's), 7.90 (br s, 1H, amide H), 8.13 (s, 1H, aromatic H), 8.26 (s, 1H, aromatic H), 9.13 (s, 1H, amine NH or —OH).

MS(CI): 279 (M+H)$^1$.

TLC: Rf (silica gel, 1:9 MeOH/CH$_2$Cl$_2$)=0.17, UV and PMA, homogeneous.

Anal Calcd for C$_{17}$H$_{14}$N$_2$O$_2$: C, 73.37; H, 5.07; N, 10.06. Found: C, 73.13; H, 5.06; N, 9.82.

EXAMPLE 9

6-[(4-Hydroxyphenyl)amino]-2-naphthalenecarboxylic acid, methyl ester

A. 6-Hydroxy-2-naphthalene carboxylic acid

To a slurry of 5.00 g (22.4 mmol, Aldrich) of 6-bromo-2-naphthol in 150 ml of dry ether at −78° was added dropwise, 16 ml (1.4M in ether, 22 mmol, Aldrich) of methyllithium solution over 10 minutes. The reaction mixture was stirred for 10 minutes, then 28 ml (1.8M in pentane, 50 mmol, Aldrich) of t-butyllithium solution was added dropwise over 15 minutes. The resulting slurry was stirred at −78° for 30 minutes then at 0° for 15 minutes. The reaction mixture was re-cooled to −78°, added into 100 g of crushed dry ice via cannula, and allowed to warm to room temperature over about ~2 hours, then added to 200 ml of 1M aqueous HCl solution and extracted with 100 ml of ethyl acetate. The organic extract was separated, washed with an additional 200 ml of H$_2$O and concentrated in vacuo to give a pale yellow solid. The crude material was dissolved in 125 ml of warm, saturated aqueous NaHCO$_3$ solution and extracted with two 50 ml portions of ethyl acetate. The aqueous phase was acidified to pH 1 with concentrated HCl. The solid which precipitated was collected on a Buchner funnel then dried under vacuum at 110° to afford 2.95 g (70%) of title compound as an off-white powder, m.p. 237°–241°.

IR(KBr) 3429 (broad, 1669, 1626, 1484, 1396, 1289, 1206 cm$^{-1}$.

270 MHz $^1$H NMR(CDCl$_3$+DMSO-d$_6$) 7.17 (m, 2H), 7.65 (d, J=8, 1H), 7.79 (d, J=10, 1H), 7.92 (dd, J=2, 1H), 8.46 (s, 1H), 9.62 (br s, 1H, —OH).

Partial 67.5 $^{13}$C NMR(CDCl$_3$/DMSO-d$_6$) 156.49, 167.37.

MS(CI): 189 (M+H)$^+$.

TLC: Rf (silica gel, 1:9 MeOH/CH$_2$Cl$_2$)=0.35, UV.

B. 6-[(4-Hydroxyphenyl)amino]-2-naphthalene carboxylic acid, methyl ester

A mixture of 300 mg (1.60 mmol) of Part A compound, 218 mg (2.00 mmol, Aldrich) of 4-aminophenol and 500 mg (4.80 mmol, Aldrich) of sodium bisulfite in 5 ml of H$_2$O was heated to 150° with rapid stirring in a sealed Pyrex tube for 24 hours. The reaction mixture was cooled, added to 50 ml of H$_2$O and extracted with 50 ml of ethyl acetate. The organic extract was separated, washed with an additional 50 ml of H$_2$O and dried (MgSO$_4$). The resulting solution was cooled in an ice-bath and treated with excess ethereal diazomethane. After 5 minutes, 1 ml of glacial acetic acid was added and the solution concentrated in vacuo to give a yellow oil. The crude oil was purified by flash chromatography (10×5.0 cm. 1:4 EtOAc/petroleum ether) followed by recrystallization (ether/petroleum ether) to afford 360 mg (77%) of title ester as yellow crystals, m.p. 174°–175°.

IR(KBr) 3393(broad), 1691, 1626, 1508, 1301, 1270, 1209, 824 cm$^{-1}$.

270 MHz $^1$H NMR(CDCl$_3$+DMSO-d$_6$) 3.92 (s, 3H, —OCH$_3$), 6.69 (s, 1H), 6.87 (d, J=9, 2H, benzene aromatics), 7.05 (m, 4H), 7.51 (d, J=9 1H), 7.72 (d, J=9, 1H), 7.87 (dd, J=2, 9, 1H), 8.39 (s, 1H, —NH— or —OH), 8.66 (s, 1H, —NH— or —OH).

67.5 MHz $^{13}$C NMR(CDCl$_3$+DMSO-d$_6$) 51.44, 105.57, 115.84, 118.71, 122.87, 123.76, 125.29, 125.43, 126.16, 130.09, 130.40, 132.63, 137.18, 146.11, 153.47, 167.09.

MS(CI): 294 (M+H)$^+$.

TLC: Rf (silica gel, 1:2 EtOAc/petroleum ether)=0.27, PMA and UV, homogeneous.

Anal Calcd for C$_{18}$H$_{15}$NO$_3$: C, 73.71; H, 5.15; N, 4.78. Found: C, 73.63; H, 5.14; N, 4.67.

EXAMPLE 10

6-[(4-Hydroxyphenyl)amino]-2-naphthalene carboxylic acid

A. 6-[(4-Hydroxyphenyl)amino]-2-naphthalene carboxylic acid, phenylbenzyl ester In a sealed thick-walled tube a rapidly stirred mixture of 300 mg (1.60 mmol) of Example 9, Part A acid, 220 mg (2.02 mmol, Aldrich) of 4-aminophenol and 500 mg (4.8 mmol, Aldrich) of sodium bisulfite in 5 ml of H$_2$O was heated to 150° C. for 25 hours. The reaction mixture was cooled, added to 50 ml of H$_2$O and extracted with two 30 ml portions of hot ethyl acetate. The organic extracts were combined, dried (MgSO$_4$) then 400 mg (2.06 mmol) of diphenyldiazomethane was added. The resulting purple solution was kept at room temperature for 7 days and finally concentrated in vacuo to give an oil. The crude oil was purified by flash chromatography (15×5.0 cm, 1:2 EtOAc/petroleum ether) to afford 530 mg (74%) of title ester as a yellow foam.

IR(KBr) 3393, 1691, 1624, 1510, 1279, 1232, 1197, 1096 cm$^{-1}$.

60 MHz $^1$H NMR(CDCl$_3$) 5.47 (br s, 1H, —NH—), 5.78 (s, 1H, benzylic methine), 6.80–8.25 (m, 20H, aromatic), 8.55 (s, 1H, —OH).

MS(CI): 446 (M+H)$^+$.

TLC: Rf (silica gel, 1:2 EtOAc/petroleum ether)+0.25, PMA and UV.

The Rf of the ester of Example 9, Part A acid under identical conditions was 0.38, UV only.

B. 6-[(4-Hydroxyphenyl)amino]-2-naphthalene carboxylic acid

A mixture of 450 mg (1.01 mmol) of Part A compound and 100 mg of 10% Pd/C catalyst in 15 ml of methanol was stirred rapidly under an atmosphere of hydrogen (balloon) for 18 hours then filtered through a plug of silica gel. The filtrate was concentrated in vacuo to give a solid. The crude solid was purified by flash chromatography (10×3.0 cm, 1:4 EtOAc/petroleum ether then 1:1 EtOAc/petroleum ether containing 1% MeOH) to afford 175 mg (62%) of title compound as a lavender solid, m.p. 252° (dec.).

IR (KBr) 3196 (broad), 1678, 1624, 1513, 1495, 1324, 1266, 1233, 1197 cm$^{-1}$.

270 MHz $^1$H NMR(DMSO-d$_6$) 6.77 (d, J=9, 2H, benzene ring), 7.08 (d, J=9, 2H, benzene ring), 7.12 (s, 1H), 7.17 (d, J=9, 1H), 7.57 (d, J=9, 1H), 7.76 (d, J=8, 1H), 7.83 (d, J=9, 1H), 8.22 (s, 1H), 8.33 (s, 1H).

MS(CI): 280 (M+H)$^+$.

TLC: Rf (silica gel, 1:9 MeOH/CH$_2$Cl$_2$)=0.33, PMA and UV, homogeneous.

The Rf of Part A compound under identical conditions was 0.70.

Anal Calcd for C$_{17}$H$_{13}$NO$_3$: C, 73.11; H, 4.69; N, 5.02. Found: C, 72.57; H, 4.84; N, 4.93.

EXAMPLE 11

4-[(6-Pentyl-2-naphthalenyl)amino]phenol

A. 6-(1-Hydroxypentyl)-2-naphthol

To a solution of 1.00 g (4.48 mmol, Aldrich) of 6-bromo-2-naphthol in 40 ml of dry ether at −78° was added dropwise 3.2 ml (1.4M in ether, 5.0 mmol) of methyllithium solution. The reaction mixture was stirred for 5 minutes then 5.0 ml (1.8M in pentane, 9.0 mmol) of t-butyllithium solution was added over 5 minutes. The resulting slurry was stirred at −78° C. for 30 minutes then at 0° for 15 minutes, re-cooled to −78° and a solution of 0.50 ml (4.7 mmol) of distilled valeraldehyde in 3 ml of ether was added dropwise over several minutes. After 5 minutes the reaction mixture was warmed to 0°, quenched with 1 ml of H$_2$O, added to 100 ml of ice-cold saturated aqueous NH$_4$Cl solution. The organic layer was separated, washed with 100 ml of H$_2$O, dried (MgSO$_4$) and concentrated in vacuo to give a dark oil. The crude oil was purified by flash chromatography (10×5.0 cm, 1:3 EtOAc/petroleum ether) to afford 590 mg (57%) of title compound as a pale yellow solid, m.p. 109°–111°.

60 MHz $^1$H NMR(CDCl$_3$/CD$_3$OD) δ0.80 (crude t, 3H, —CH$_3$), 1.03–2.20 (m, 6H, —(CH$_2$)$_3$CH$_3$), 3.72 (br s, 2H, —OH), 4.73 (t, J=6, 1H, benzylic methine), 6.90–7.83 (m, 6H, aromatic).

TLC: Rf (silica gel, 1:2 EtOAc/petroleum ether)=0.29, PMA and UV. The Rf of 6-bromo-2-naphthol under identical conditions was 0.53.

B. 6-Pentyl-2-naphthol

To a slurry of 500 mg (2.17 mmol) of Part A compound in 3 ml of triethylsilane (Aldrich) was added 3 ml of trifluoroacetic acid dropwise at room temperature. The reaction mixture was stirred for 30 minutes then concentrated in vacuo to give a solid. The crude solid was washed with petroleum ether then purified by flash chromatography (silica gel, 10×3 cm, 1:5 EtOAc/petroleum ether) and recrystallized (benzene/petroleum ether) to afford 435 mg (94%) of title compound as white crystals, m.p. 94°–95°.

IR(KBr) 3287, 2851, 1642, 1609, 1510, 1467, 1453, 1288, 1228, 1157 cm$^{-1}$.

270 MHz $^1$H NMR(CDCl$_3$) δ0.89 (t, J=7, 3H, —CH$_3$), 1.34 (m, 4H, —(CH$_2$)$_2$CH$_3$), 1.68 (m, 2H, —CH$_2$(CH$_2$)$_2$CH$_3$), 2.72 (t, J=8, 2H, benzylic —CH$_2$—), 4.83 (s, 1H, —OH), 7.06 (dd, J=3, 9, 1H), 7.11 (d, J=2, 1H), 7.28 (dd, J=2, 9, 1H), 7.53 (s, 1H), 7.59 (d, J=8, 1H), 7.67 (d, J=8, 1H).

MS(CI): 215 (M+H)$^+$.

TLC: Rf (silica gel, 1:3 EtOAc/petroleum ether)=0.46, UV and PMA; the Rf of Part A compound under identical conditions was 0.17.

C. 4-[(6-Pentyl-2-naphthalenyl)amino]phenol

A mixture of 275 mg (1.29 mmol) of Part B compound, 185 mg (1.70 mmol, Aldrich) of 4-aminophenol and 1.00 g (9.6 mmol, Aldrich) of sodium bisulfite in 6 ml of 1:2 dioxane/water was heated to 150° with rapid stirring in a closed tube for 48 hours. The reaction mixture was cooled, added to 25 ml of H$_2$O and extracted with 25 ml of ethyl acetate. The organic extract was washed with 25 ml of H$_2$O, dried (MgSO$_4$) and concentrated in vacuo to give a solid. The crude material was purified by flash chromatography (silica gel, 12×3.0 cm, 1:5 EtOAc/petroleum ether) then recrystallized (EtOAc/petroleum ether) to afford 48 mg (12%) of title compound as white crystals, m.p. 134°–135°.

IR(KBr) 3402, 2924, 1633, 1608, 1516, 1315, 1252, 870, 817 cm$^{-1}$.

270 MHz $^1$H NMR(CDCl$_3$) δ0.89 (t, J=7, 3H, —CH$_3$), 1.34 (m, 4H, —(CH$_2$)$_2$CH$_3$), 1.68 (m, 2H, —CH$_2$(CH$_2$)$_2$CH$_3$), 2.70 (t, J=7, 2H, benzylic methylene), 4.54 (br s, 1H, —OH or NH), 5.57 (br s, 1H, —OH or NH), 6.81 (d, J=9, 2H, aromatic), 7.00–7.30 (m, 5H, aromatic), 7.48 (s, 1H, aromatic), 7.51 (d, J=8, 1H, aromatic), 7.63 (d, J=8, 1H, aromatic).

MS(CI): 306 (M+H)$^+$.

TLC: Rf (silica gel, 1:3 EtOAc/petroleum ether)=0.26, PMA and UV, homogeneous. The Rf of Part B compound under identical conditions was 0.48.

Anal Calcd for C$_{21}$H$_{23}$NO: C, 82.58; H, 7.59; N, 4.59. Found: C, 82.70; H, 7.61; N, 4.27.

EXAMPLE 12

4-[(6-Bromo-2-naphthalenyl)amino]phenol

A mixture of 334 mg (1.50 mmol, Aldrich) of 6-bromo-2-naphthol, 218 mg (2.00 mmol, Aldrich) of 4-aminophenol, and 1.0 g of sodium bisulfite in 5 ml of H$_2$O was heated to 150° in a closed Pyrex tube for 76 hours. The reaction was cooled, added to 25 ml of H$_2$O and extracted with 25 ml of ethyl acetate. The organic extract was dried (MgSO$_4$) and concentrated in vacuo to give a solid. The crude solid was purified by flash chromatography (10×5.0 cm, 1:4 EtOAc/petroleum ether) followed by recrystallization (EtOAc/petroleum ether) to afford 330 mg (70%) of title compound as small grey-white crystals, m.p. 179°–180°.

IR(KBr) 3405 (broad), 1627, 1590, 1525, 1315, 1251, 869, 815 cm$^{-1}$.

270 MHz $^1$H NMR (CDCl$_3$/DMSO-d$_6$) δ6.06 (s, 1H, —NH—), 6.86 (m, 2H), 7.08 (m, 4H), 7.39 (m, 2H), 7.56 (d, J=8, 1H), 7.80 (s, 1H), 8.40 (s, 1H, —OH).

MS(CI): 314, 316 (M+H)$^+$.

TLC: Rf (silica gel, 1:4 EtOAc/petroleum ether)=0.12, PMA and UV. The Rf of 6-bromo-2-naphthol under identical conditions was 0.25.

Anal Calcd for C$_{16}$H$_{12}$BrNO: C, 61.17; H, 3.85; N, 4.46; Br, 25.43. Found: C, 61.13; H, 3.84; N, 4.38; Br, 25.42.

EXAMPLE 13

4-[(6-Iodo-2-naphthalenyl)amino]phenol

A. 6-Iodo-2-methoxynaphthalene

To a solution of 1.00 g (4.22 mmol, Aldrich) of 6-bromo-2-methoxynaphthalene in 10 ml of dry THF at −78° was added dropwise 4.5 ml (1.4M in pentane, 6.3 mmol, Aldrich) of t-butyllithium solution over 10 minutes. The reaction mixture was stirred at −78° for 30 minutes then at 0° for 15 minutes. The resulting yellow solution was re-cooled to 31 78° then 1.20 g (4.72 mmol, Aldrich) of iodine was added in one portion. The reaction mixture was warmed to room temperature, stirred for 1 hour then added to 50 ml of H$_2$O and extracted with 50 ml of ethyl acetate. The organic extract was washed with an additional 50 ml of H$_2$O, dried (MgSO$_4$) and concentrated in vacuo to give a solid. The crude solid was recrystallized (EtOAc/petroleum ether) to afford 805 mg (67%) of title compound as pale yellow flakes, m.p. 142°–143°.

IR(KBr) 1622, 1578, 1494, 1264, 1212, 1165, 1029, 898, 854, 817, 476, 465 cm$^{-1}$.

270 MHz $^1$H NMR(CDCl$_3$) 3.89 (s, 3H, —OCH$_3$), 7.05 (d, J=3, 1H), 7.12 (dd, J=3, 9, 1H), 7.45 (d, J=8, 1H), 7.59 (d, J=9, 1H), 7.64 (dd, J=2, 8, 1H), 8.11 (s, 1H).

67.5 MHz $^{13}$C NMR (CDCl$_3$) 55.32, 88.05, 105.8, 119.5, 128.4 (s), 130.6, 133.4, 134.8, 136.3, 158.0.

MS(CI): 285 (M+H)$^{30}$.

TLC: Rf (silica gel, 1:4 ether/petroleum ether)=0.49, UV and PMA, homogeneous.

The Rf of 6-bromo-2-methoxynaphthalene under identical conditions was 0.58.

B. 6-Iodo-2-naphthol

To a solution of 475 ml (1.67 mmol) of Part A compound in 10 ml of dry CH$_2$Cl$_2$ at −78° was added 2.0 ml (1.0M in CH$_2$Cl$_2$, 2.0 mmol, Aldrich) of boron tribromide solution. The reaction mixture was allowed to warm to room temperature, stirred for 2 hours then added to 50 ml of saturated aqueous NaHCO$_3$ solution and extracted with 35 ml of ethyl acetate. The organic layer was separated, washed with 25 ml of H$_2$O, dried (MgSO$_4$) and concentrated in vacuo to give a solid. The crude material was purified by flash chromatography (10×3.0 cm, 1:4 EtOAc/petroleum ether) to afford 433 mg (96%) of title compound as a white solid, m.p. 136°–138°.

IR(KBR) 3282, 1625, 1586, 1501, 1452, 1245, 1201, 900, 881, 858, 493, 471 cm$^{31\ 1}$.

270 MHz $^1$H NMR (CDCl$_3$) 5.00 (s, 1H, —OH), 7.10 (m, 2H), 7.41 (d, J=9, 1H), 7.63 (d, J=9, 1H), 7.64 (dd, J=2, 9, 1H), 8.14 (d, J=1, 1H). MS(CI): 271 (M+H)$^+$.

TLC: Rf (silica gel, 1:4 EtOAc/petroleum ether)=0.32, PMA and UV, homogeneous.

The Rf of Part A compound under identical conditions was 0.69.

C. 4-[(6-Iodo-2-naphthalenyl)amino]phenol

A rapidly stirred mixture of 400 mg (1.48 mmol) of Part B compound, 300 mg (2.75 mmol, Aldrich) of 4-aminophenol, 500 mg (4.80 mmol, Aldrich) of sodium bisulfite and 5 ml of H$_2$O was heated to 160° for 72 hours in a sealed tube. The reaction was cooled, added to 50 ml of H$_2$O and extracted with two 25 ml portions of ethyl acetate. The combined organic extracts were dried (MgSO$_4$) and concentrated in vacuo to give a solid. The crude solid was purified by flash chromatography (15×3.0 cm, 1:2 EtOAc/petroleum ether) followed by recrystallization (EtOAc/petroleum ether) to afford 425 mg (80%) of title compound as light grey crystals, m.p. 194°–195° (dec.).

IR(KBr) 3409 (broad), 1625, 1583, 1520, 1314, 1250, 868, 816, 475 cm$^{31\ 1}$.

270 MHz $^1$H NMR(CDCl$_3$+DMSO-d$_6$) 6.40 (s, 1H, —NH—), 6.85 (dd, J=2, 6, 2H, benzene aromatics), 7.08 (m, 4H), 7.27 (d, J=9, 1H), 7.51 (d, J=8, 2H), 8.00 (s, 1H), 8.59 (s, 1H, —OH).

67.5 $^{13}$C NMR(CDCl$_3$+DMSO-d$_6$) 85.64, 106.3, 115.8, 119.0, 123.3, 127.4, 129.3, 133.2, 133.3, 134.0, 135.6, 144.3, 153.1.

MS(CI): 362 (M+H)$^+$.

TLC: Rf (silica gell, 1:2 EtOAc/petroleum ether)=0.35, PMA and UV, homogeneous.

The Rf of Part B compound under identical conditions was 0.48.

Anal Calcd for $C_{16}H_{12}INO$: C, 53.21; H, 3.35; N, 3.88; I, 35.13. Found: C, 53.60; H, 3.61; N, 3.75; I, 35.09.

EXAMPLE 14

4-[2-Naphthalenylmethyl)amino]phenol

A solution of 1.00 g (4.50 mmol, Aldrich) of 2-(bromomethyl)naphthalene, 2.46 g (22.6 mmol, 5 eq., Aldrich) of 4-aminophenol and 1.51 g (18.0 mmol, 4 eq.) of sodium bicarbonate in 12 ml of dry HMPA was stirred at 0° C. for 60 minutes. Water was added and this was extracted with EtOAc. The organic layers were combined, dried ($MgSO_4$) and concentrated in vacuo. Purification via flash chromatography (silica gel, 1:5 EtOAc/petroleum ether) afforded 800 mg (71%) of title compound as a white solid: m.p. 120°–121° C.

IR(KBr) 3491, 3327, 1600, 1509, 1421, 1367, 1336, 1307, 1227, 1112, 821, 746 $cm^{-1}$.

270 MHz $^1H$ NMR ($CDCl_3$) 4.10 (br s, 2H, —NH and OH), 4.43 (s, 2H, H—N—$CH_2$), 6.58 (d, J=9 Hz, 2H, phenol H's), 6.70 (d, J=9 Hz, 2H, phenol H's), 7.43 (m, 3H, aromatic H's), 7.80 (m, 4H, aromatic H's).

MS(CI): 250 $(M+H)^+$.

TLC: Rf (silica gel, 1:1 EtOAc/petroleum ether)=0.52, UV and PMA, homogeneous.

Anal Calcd for $C_{17}H_{15}NO$: C, 81.89; H, 6.07; N, 5.62. Found: C, 81.87; H, 6.10; N, 5.68.

EXAMPLE 15

N-(4-Hydroxyphenyl)-N-(6-hydroxy-2-naphthalenyl)acetamide

A solution of 830 mg (3.30 mmol) of 6-[(4-hydroxyphenyl)amino]-2-naphthalenol (prepared as described in Example 3) and 840 ul (6.60 mmol, 2 eq.) of dimethylaniline in 15 ml of dry $CH_2Cl_2$ and 5 ml of dry THF was stirred at 0° C., then 415 ul (5.80 mmol, Mallinckrodt) of acetyl chloride was added dropwise. After 50 minutes, 1N aqueous HCl was added and this was extracted with EtOAc. The organic layers were washed with 1N aqueous HCl, dried ($MgSO_4$) and concentrated in vacuo. The aqueous layers were extracted with hot EtOAc and the organic layers were combined, dried ($MgSO_4$) and concentrated in vacuo. Purification of all the organic phases was accomplished via flash chromatography (1:2, 1:1 EtOAc/petroleum ether) and recrystallization (aqueous MeOH) afforded 97 mg (10%) of title compound as pale orange crystals: m.p. 255° C.

IR(KBr) 3349, 2799, 2674, 2597, 1606, 1592, 1508, 1472, 1402, 1250, 993, 881, 858, 842 $cm^{-1}$.

270 MHz $^1H$ NMR(DMSO-$d_6$) δ1.93 (s, 3H, $COCH_3$), 6.76 (s, 2H, aromatic H's), 7.10–7.32 (br m, 4H, aromatic H's), 7.67 (s, 4H, aromatic H's), 9.69 (br s, 2H, —NH— and —OH—).

MS(CI): 294 $(M+H)^+$.

TLC: Rf (silica gel, 3:1 EtOAc/petroleum ether)=0.38, UV and PMA, homogeneous.

Anal Calcd for $C_{18}H_{15}NO_3$: C, 73.70; H, 5.15; N, 4.77. Found: C, 73.49; H, 5.22; N, 4.65.

EXAMPLE 16

N-(4-Hydroxyphenyl)-N-(6-methoxy-2-naphthalenyl)acetamide

To a solution of 190 mg (0.72 mmol) of 4-[(6-methoxy-2-naphthyl)amino]phenol (prepared as described in Example 2) and 0.50 ml of pyridine (dried over KOH) in 4 ml of dry $CH_2Cl_2$ at 0° was added dropwise over 5 minutes 55 ul (0.77 mmol) of acetyl chloride. The reaction mixture was stirred for 30 minutes then added to 25 ml of 1N aqueous HCl solution and extracted with 25 ml of warm ethyl acetate. The organic extract was washed with an additional 25 ml of 1M aqueous HCl solution, dried ($MgSO_4$) and concentrated in vacuo to give a solid. The crude solid was purified by flash chromatography (silica gel, 10×3.0 cm, 1:1 EtOAc/petroleum ether) followed by recrystallization (EtOAc/petroleum ether) to afford 145 mg (66%) of title compound as white crystals, m.p. 187°–188°.

IR(KBr) 3100 (broad), 1642, 1605, 1511, 1463, 1391, 1261, 1241, 1222, 1169, 1031 $cm^{-1}$.

270 MHz $^1H$ NMR (DMSO-$d_6$) δ1.94 (s, 3H, acetyl $CH_3$), 3.86 (s, 3H, —$OCH_3$), 6.60–7.95 (m, 10H, aromatic), 9.60 (br s, 1H, —OH).

MS(CI): 308 $(M+H)^+$.

TLC: Rf (silica gel, 1:1 EtOAc/petroleum ether)=0.21, PMA and UV, homogeneous The Rf of Example 2 compound under identical conditions was 0.60.

Anal Calcd for $C_{19}H_{17}NO_3$: C, 74.25; H, 5.58; N, 4.56. Found: C, 74.38; H, 5.68; N, 4.56.

EXAMPLE 17

4-[(6-Methoxy-2-naphthyl)methylamino[phenol

A.

2-[(4-Benzyloxyphenyl)amino]-6-methoxynaphthalene

The oil was removed from 100 mg (50% in oil, 2.1 mmol, Alfa) of sodium hydride dispersion by washing with three portions of petroleum ether then the residue was covered with 10 ml of dry THF. A total of 530 mg (2.00 mmol) of 4-[(6-methoxy-2-naphthyl)amino]phenol (prepared as described in Example 2) was added to the resulting mixture in several portions. The deep purple reaction mixture was stirred for an additional 10 minutes until hydrogen evolution ceased then 1 ml of sieve-dried DMF was added, followed by 240 ul (2.02 mmol, Aldrich) of benzyl bromide. The solution was heated to 50° for 1 hour, cooled, added to 50 ml of $H_2O$ and extracted with 50 ml of ethyl acetate. The organic extract was washed with two additional portions of $H_2O$, dried ($MgSO_4$) and concentrated in vacuo to give 690 mg (97%) of crude title compound as a lavender solid, m.p. 155°–157°.

60 MHz $^1H$ NMR($CDCl_3$) 3.85 (s, 3H, —$OCH_3$), 5.03 (s, 2H, —$OCH_2Ph$), 6.77–7.80 (m, 16H).

TLC: Rf (silica gel), 1:2 EtOAc/petroleum ether)=0.47, PMA and UV, homogeneous.

The Rf of Example 2 compound under identical conditions was 0.26.

B.

2-[(4-Benzyloxyphenyl)methylamino]-6-methoxynaphthalene

In a stoppered flask a mixture of 675 mg (1.90 mmol) of Part A compound, 235 ul (3.80 mmol, MCB) of iodomethane and 400 mg (4.76 mmol) of powdered sodium bicarbonate in 5 ml of dry HMPA was heated to 50° for 18 hours. The reaction was cooled, added to 25 ml of $H_2O$ and extracted with 25 ml of dichloromethane. The organic extract was separated, washed with three 25 ml portions of $H_2O$, dried ($Na_2SO_4$) and concentrated in vacuo to give a solid. The crude material was solubilized in dichloromethane and filtered through a pad of neutral alumina (5×3 cm, activity I, $CH_2Cl_2$ elution). The filtrate was concentrated in vacuo to afford 598 mg (85%) of title compound as a pale pink solid, m.p. 139°-141°.

60 MHz $^1$H NMR(CDCl$_3$) 3.30 (s, 3H, —NCH$_3$), 3.83 (s, 3H, —OCH$_3$), 5.00 (s, 2H, —OCH$_2$Ph), 6.70-7.70 (m, 15H).

MS(CI): 370 (M+H)$^+$.

TLC: Rf (silica gel, 1:4 EtOAc/petroleum ether)=0.53, PMA and UV, homogeneous.

The Rf of Part A compound under identical conditions was 0.33.

C. 4-[(6-Methoxy-2-naphthyl)methylamino]phenol

To 40 ml of anhydrous methanol cooled in an ice-bath was added dropwise 0.50 ml (7.0 mmol) of acetyl chloride. The solution was stirred for 15 minutes then under argon, 150 mg of 10% palladium on charcoal catalyst was added in one portion. The mixture was warmed to room temperature then 560 mg (1.52 mmol) of Part B compound was added and the reaction stirred rapidly under an atmosphere of hydrogen (balloon) for 3 hours. The resulting mixture was filtered through a small column (4×2 cm) of sand and the eluant refiltered through a polycarbonate filter. The filtrate was concentrated in vacuo and the residue partitioned between 50 ml of saturated aqueous NaHCO$_3$ solution and 50 ml of ethyl acetate. The organic extract was separated and the aqueous layer extracted with 25 ml of ethyl acetate. The organic extracts were combined in vacuo to give a solid. The crude solid was purified by flash chromatography (10×3.0 cm, 1:4 EtOAc/petroleum ether) followed by recrystallization (EtOAc/petroleum ether) to afford 320 mg (75%) of title compound as pale yellow-green crystals, m.p. 139°-140°.

IR(KBr) 3307, 1605, 1514, 1463, 1391, 1244, 1205, 1166, 1120, 1030, 853, 827 cm$^{-1}$.

270 MHz $^1$H NMR(CDCl$_3$) 3.32 (broadened s, 3H, —NCH$_3$), 3.89 (s, 3H, —OCH$_3$), 4.61 (s, 1H, —OH), 6.80 (d, J=9, 2H, phenol aromatics), 7.05 (m, 6H, aromatics), 7.53 (d, J=10, 1H, aromatic), 7.57 (d, J=9, 1H, aromatic).

MS(CI): 280 (M+H)$^+$.

TLC: Rf (silica gel, 1:4 EtOAc/petroleum ether)=0.18, PMA and UV, homogeneous.

The Rf of Part B compound identical conditions was 0.51.

Anal Calcd for C$_{18}$H$_{17}$NO$_2$: C, 77.40; H, 6.13; N, 5.01. Found: C, 77.51; H, 6.14; N, 4.94.

EXAMPLE 18

4-(6-Quinolinylamino)phenol

A. 6-Hydroxyquinoline

A solution of 2.50 g (15.7 mmol, Aldrich) of 6-methoxyquinoline in 10 ml of 48% aqueous HBr was refluxed for 24 hours. The reaction mixture was cooled, added slowly to a 150 ml stirred solution of saturated aqueous sodium bicarbonate and then extracted with two 100 ml portions of ethyl acetate. The organic extracts were combined, dried (MgSO$_4$) and concentrated in vacuo to give a solid. The crude material was recrystallized (EtOAc/petroleum ether) to afford 1.95 g (84%) of title compound as white crystals, m.p. 194°-195°.

IR(KBr) ~3100-2500 (broad), 1637, 1579, 1500, 1417, 1377, 1321, 1268, 1242, 1228, 1159, 1127, 921, 838, 791, 772 cm$^{-1}$.

270 MHz $^1$H NMR(CDCl$_3$+DMSO-d$_6$) δ7.13 (d, J=3, 1H), 7.31 (dd, J=4, 8, 1H), 7.35 (dd, J=2, 8, 1H), 7.91 (d, J=8, 1H), 7.99 (d, J=7, 1H), 8.67 (dd, J=2, 4, 1H), 9.77 (broad s, 1H, —OH).

67.5 MHz $^{13}$C NMR(CDCl$_3$+DMSO-d$_6$) 107.6, 120.2, 121.3, 128.7, 129.4, 133.4, 142.5, 146.0, 154.8.

MS(CI): 148 (M+H)$^+$.

TLC: Rf (silica gel, 1:1 EtOAc/petroleum ether)=0.26, UV, homogeneous.

The Rf of 6-methoxyquinoline under identical conditions was 0.39.

B. 4-(6-Quinolinylamino)phenol

A rapidly stirred solution of 300 mg (2.04 mmol) of Part A compound, 272 mg (2.50 mmol, Aldrich) of 4-aminophenol and 500 mg (4.8 mmol, Aldrich) of sodium bisulfite in 5 ml of H$_2$O was heated to 160° C. in a closed tube for 20 hours. The reaction mixture was cooled, added to 50 ml of H$_2$O and extracted with two 50 ml portions of hot ethyl acetate. The organic extracts were combined, dried (MgSO$_4$) and concentrated in vacuo to give an orange solid. The crude material was purified by flash chromatography (20×5.0 cm, 1:1:1 EtOAc/CH$_2$Cl$_2$/petroleum ether) to afford 310 mg (64%) of title compound as a yellow solid, m.p. ~235° C. (dec.).

IR(KBr) 3375, ~3050-2400 (broad), 1624, 1512, 1469, 1383, 1250, 833 cm$^{-1}$.

270 MHz $^1$H NMR(CDCl$_3$+DMSO-d$_6$) δ6.79 (d, J=8, 2H, phenol aromatics), 7.08 (m, 3H), 7.24 (dd, J=4, 8, 1H), 7.37 (dd, J=3, 9, 1H), 7.80 (m, 2H), 7.88 (d, J=8, 1H), 8.52 (dd, J=2, 4, 1H), 8.98 (broad s, 1H).

67.5 MHz $^{13}$C NMR(CDCl$_3$+DMSO-d$_6$) 103.0, 114.3, 119.6, 120.6, 121.2, 128.1, 131.9, 141.5, 142.9, 144.2, 151.5.

MS(CI): 237 (M+H)$^+$.

TLC: Rf (silica gel, 2:1:1 EtOAc/CH$_2$Cl$_2$/petroleum ether)=0.17, PMA and UV, homogeneous. The Rf of Part A compound and 4-aminophenol under identical conditions was 0.22.

Anal Calcd for C$_{15}$H$_{12}$N$_2$O: C, 76.25; H, 5.12; N, 11.86. Found: C, 75.90; H, 5.22; N, 11.81.

EXAMPLES 19 TO 42

Following the procedures as outlined in the Specification and the working Examples, the following additional compounds in accordance with the present invention may be prepared.

| Ex. No. | $R^4$ | $R^1$(position) | $R^3$ | $(CH_2)_m$ | $R^2$(position) |
|---|---|---|---|---|---|

Structure:

$R^1$ at positions 2,3 of phenyl ring with $OR^4$ at position 1; $R^3-N-(CH_2)_m-$ at position 4 connecting to naphthalene (positions 1-8) with $R^2$.

| Ex. No. | $R^4$ | $R^1$(position) | $R^3$ | $(CH_2)_m$ | $R^2$(position) |
|---|---|---|---|---|---|
| 19. | H | H | $C_2H_5$ | $CH_2$ | $C_2H_5$ (6) |
| 20. | $CH_3$ | $C_2H_5$ (3) | H | $(CH_2)_2$ | $C_6H_5$ (7) |
| 21. | $CH_3\overset{O}{\underset{\|}{C}}$ | $C_6H_5$ (2) | $C_3H_7\overset{O}{\underset{\|}{C}}$ | $(CH_2)_3$ | OH (6) |
| 22. | H | OH (3) | $C_6H_5\overset{O}{\underset{\|}{C}}$ | $(CH_2)_4$ | $HOCH_2O-$ (7) |
| 23. | $C_2H_5$ | $HO(CH_2)_2O$ (2) | H | $(CH_2)_5$ | $C_2H_5S$ (6) |
| 24. | $C_2H_5\overset{O}{\underset{\|}{C}}$ | $C_2H_5S$ (3) | H | $-CH_2-\overset{CH_3}{\underset{\|}{CH}}-$ | $C_3H_7O$ (8) |
| 25. | H | $CH_3O$ (6) | $C_3H_7$ | $-CH_2-\overset{CH_3}{\underset{\underset{CH_3}{\|}}{\overset{\|}{C}}}-$ | $CH_3CO$ (7) |
| 26. | $C_3H_7$ | H | $C_4H_9\overset{O}{\underset{\|}{C}}$ | $CH_2$ | $C_6H_5\overset{O}{\underset{\|}{C}}O$ (3) |
| 27. | $C_3H_7\overset{O}{\underset{\|}{C}}$ | $C_2H_5CO$ (3) $\overset{O}{\underset{\|}{}}$ | $C_6H_5\overset{O}{\underset{\|}{C}}$ | $(CH_2)_2$ | Cl (4) |
| 28. | H | $C_6H_5\overset{O}{\underset{\|}{C}}O$ (2) | $C_6H_{13}$ | $(CH_2)_3$ | $CO_2H$ (5) |
| 29. | $C_4H_9$ | Cl (5) | $C_5H_{11}$ | $-\overset{CH_3}{\underset{\|}{CH}}-$ | $C_2H_5\overset{O}{\underset{\|}{O C}}$ (6) |
| 30. | $C_4H_9\overset{O}{\underset{\|}{C}}$ | $CO_2H$ (2) | $C_4H_9\overset{O}{\underset{\|}{C}}$ | — | $NH_2\overset{O}{\underset{\|}{C}}$ (6) |
| 31. | H | $CH_3O\overset{O}{\underset{\|}{C}}$ (3) | H | — | $CH_3$ (6) |
| 32. | $C_5H_{11}$ | $NH_2\overset{O}{\underset{\|}{C}}-$ (6) | H | — | $C_2H_5$ (7) |
| 33. | $C_5H_{11}\overset{O}{\underset{\|}{C}}$ | $CH_3\overset{O}{\underset{\|}{C}}NH$ (3) | $CH_3$ | — | H |
| 34. | H | $C_6H_5\overset{O}{\underset{\|}{C}}NH$ (5) | H | — | H |
| 35. | $C_6H_{13}$ | H | $C_2H_5$ | $CH_2$ | $C_3H_7$ (5) |
| 36. | $C_6H_{13}\overset{O}{\underset{\|}{C}}$ | H | H | $(CH_2)_2$ | $C_5H_{11}$ (6) |

-continued

| Ex. No. | R⁴ | R¹(position) | R³ | (CH₂)ₘ | R²(position) |
|---|---|---|---|---|---|

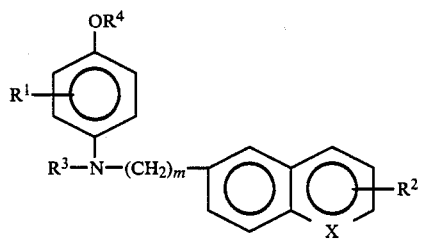

| 37. | H | $C_2H_5S$ (3) | H | $CH_2$ | Cl (4) |
| 38. | $C_2H_5$ | $CH_3O$ (6) | $C_4H_9$ | $(CH_2)_3$ | $CO_2H$ (5) |
| 39. | $C_3H_7\overset{O}{\underset{\|}{C}}$ | H | $C_5H_{11}\overset{O}{\underset{\|}{C}}$ | — | $C_2H_5\overset{O}{\underset{\|}{C}}$ (3) |
| 40. | H | $C_6H_5\overset{O}{\underset{\|}{C}}O$ (2) | H | $-CH_2-\underset{\underset{CH_3}{\|}}{CH}-$ | $C_3H_7O\overset{O}{\underset{\|}{C}}$ (5) |
| 41. | $C_7H_{15}$ | Cl (6) | $CH_3$ | $(CH_2)_6$ | $NH_2\overset{O}{\underset{\|}{C}}$ (2) |
| 42. | $C_3H_7$ | $CO_2H$ (5) | $C_6H_5\overset{O}{\underset{\|}{C}}$ | $(CH_2)_4$ | $CH_3O$ (7) |

What is claimed is:

1. A compound having the structure wherein m is 0 to 5; X is N; R¹ is H, lower alkyl, aryl, hydroxy, hydroxyalkyleneoxy, alkylthio, alkoxy, alkanoyloxy, aryloxy, halo, carboxy, alkoxycarbonyl or amido and R² may be H, lower alkyl, aryl and halo; R³ is H and lower alkyl; and R⁴ is H, lower alkyl or alkanoyl, and including pharmaceutically acceptable acid-addition salts thereof.

2. The compound as defined in claim 1 wherein R⁴ is H.

3. The compound as defined in claim 2 wherein R¹ is H.

4. The compound as defined in claim 1 wherein R³ is H and m is 0.

5. The compound as defined in claim 1 having the name 4-(6-quinolinylamino)phenol.

6. A composition for inhibiting allergic conditions mediated by leukotrienes in a mammalian species, comprising an effective amount of a compound as defined in claim 1 or a pharmaceutically acceptable salt thereof, and a pharmaceutically acceptable carrier thereof.

* * * * *